US010640487B2

(12) United States Patent
Ceric et al.

(10) Patent No.: US 10,640,487 B2
(45) Date of Patent: May 5, 2020

(54) SOLID STATE FORMS OF NILOTINIB SALTS

(71) Applicant: Teva Pharmaceuticals USA, Inc., North Wales, PA (US)

(72) Inventors: Helena Ceric, Zagreb (HR); Igor Avdejev, Zagreb (HR); Edi Topic, Malinska (HR)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 0 days.

(21) Appl. No.: 16/084,357

(22) PCT Filed: Mar. 13, 2017

(86) PCT No.: PCT/US2017/022072
§ 371 (c)(1),
(2) Date: Sep. 12, 2018

(87) PCT Pub. No.: WO2017/160703
PCT Pub. Date: Sep. 21, 2017

(65) Prior Publication Data
US 2019/0071426 A1   Mar. 7, 2019

Related U.S. Application Data

(60) Provisional application No. 62/307,841, filed on Mar. 14, 2016, provisional application No. 62/418,745, filed on Nov. 7, 2016.

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01); *C07B 2200/13* (2013.01)

(58) Field of Classification Search
CPC .................................................. C07D 401/14
See application file for complete search history.

(56) References Cited

U.S. PATENT DOCUMENTS

| 7,799,782 B2 * | 9/2010 | Munson | C07D 231/56 |
| | | | 514/234.5 |
| 2013/0158059 A1 * | 6/2013 | Piran | A61K 31/506 |
| | | | 514/275 |

FOREIGN PATENT DOCUMENTS

| WO | 2007/015870 A2 | 2/2007 |
| WO | 2007/015871 A1 | 2/2007 |
| WO | 2010/054056 A2 | 5/2010 |
| WO | 2011/163222 A1 | 12/2011 |
| WO | 2014/060449 A1 | 4/2014 |

OTHER PUBLICATIONS

Brittain's publication, crystalline and pharmaceutical composition, 1999, pp. 348-361.*

* cited by examiner

*Primary Examiner* — Rei Tsang Shiao
(74) *Attorney, Agent, or Firm* — BakerHostetler

(57) ABSTRACT

The present disclosure relates to solid state forms of Nilotinib fumarate and Nilotinib hydrochloride L-tartaric acid co-crystals, processes for preparation thereof, pharmaceutical compositions thereof, and methods of use thereof.

18 Claims, 11 Drawing Sheets

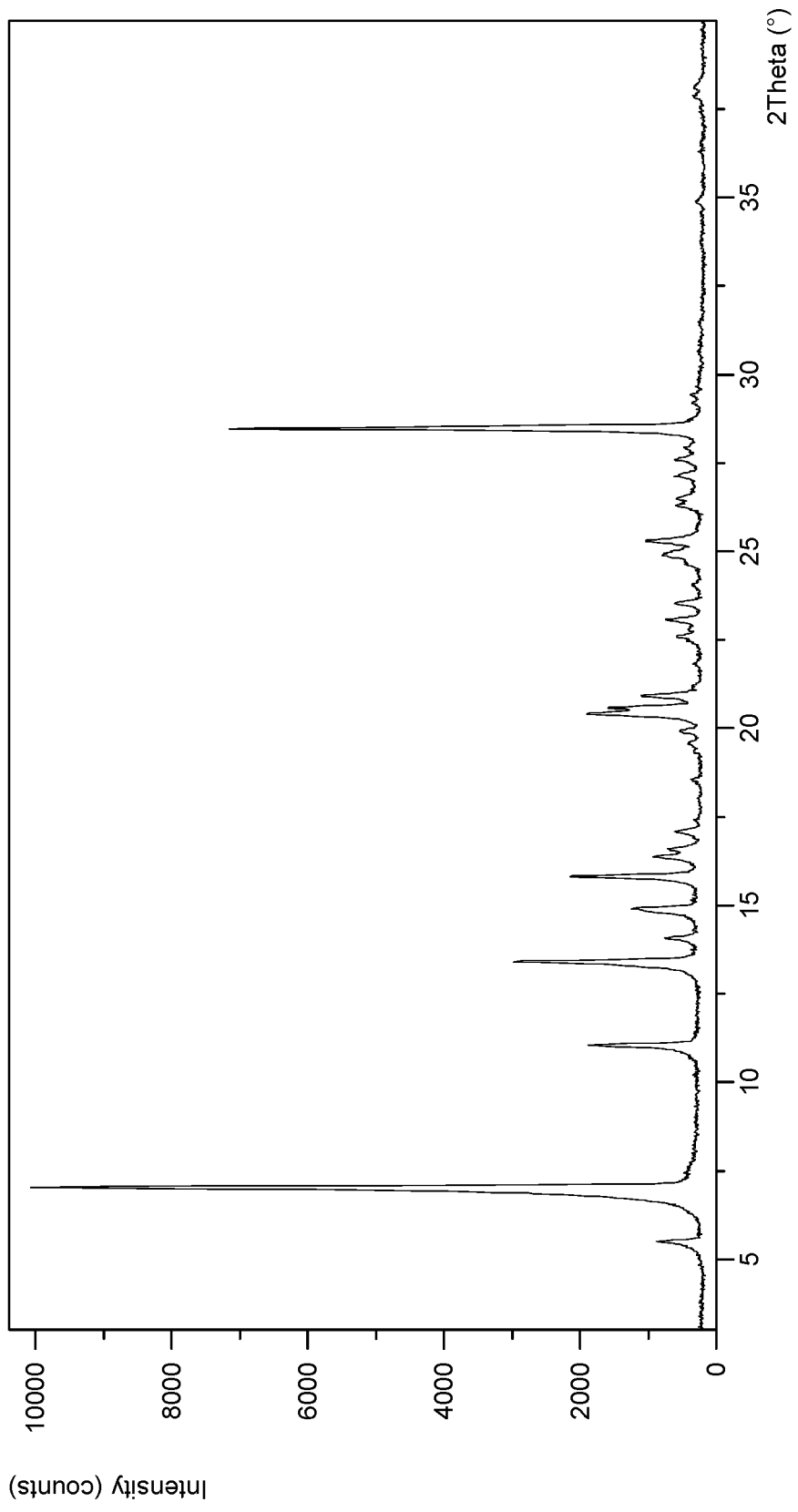
Figure 1: An X-ray powder diffraction pattern of Nilotinib fumarate Form III

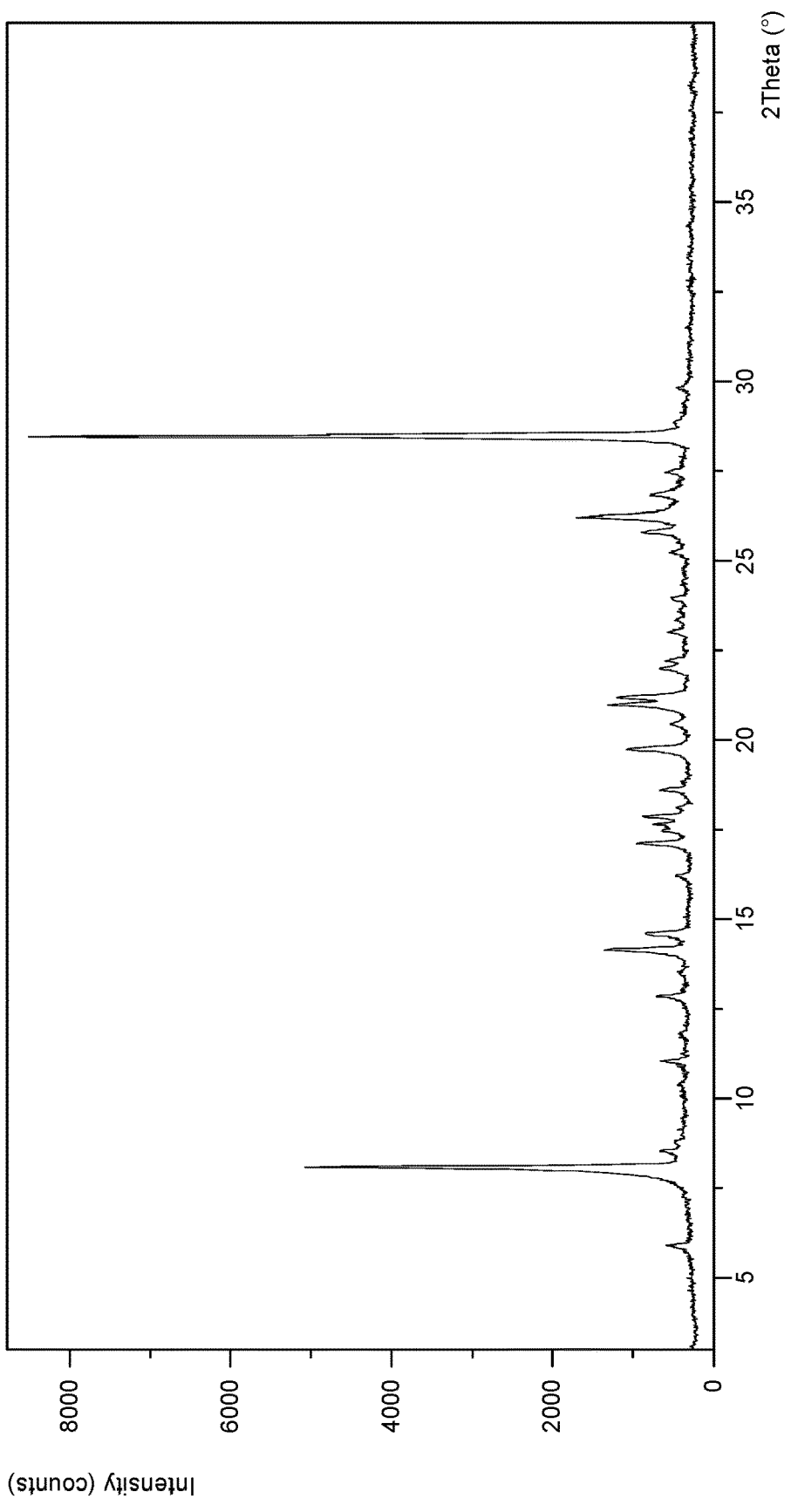
Figure 2. XRPD of Nilotinib hydrochloride L-tartaric acid co-crystal Form I
* Peak at 28.4°2θ corresponds to Si

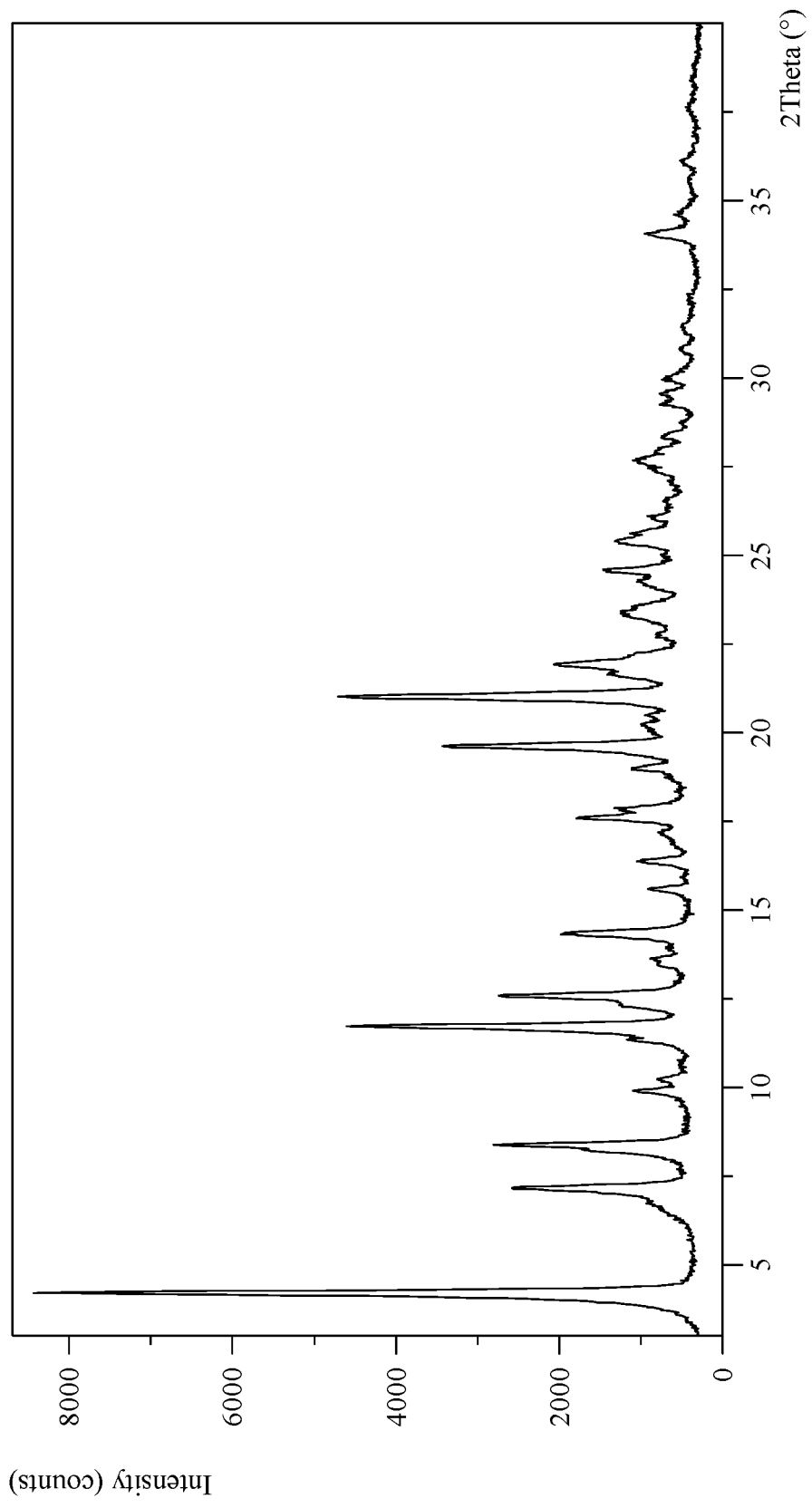
Figure 3. XRPD of Nilotinib hydrochloride L-tartaric acid co-crystal Form II

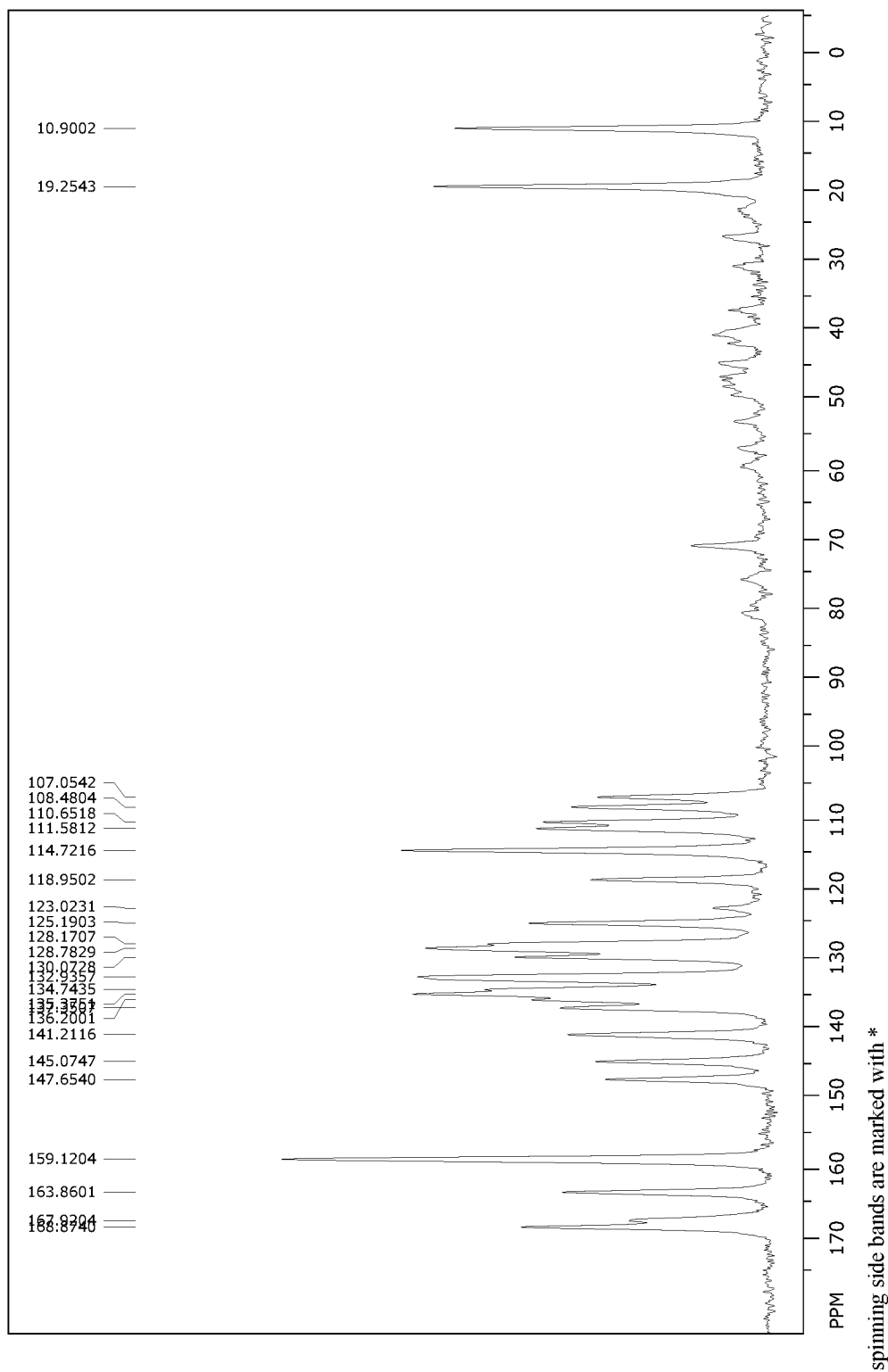
Figure 4. A solid state $^{13}$C NMR spectrum of Nilotinib fumarate Form III

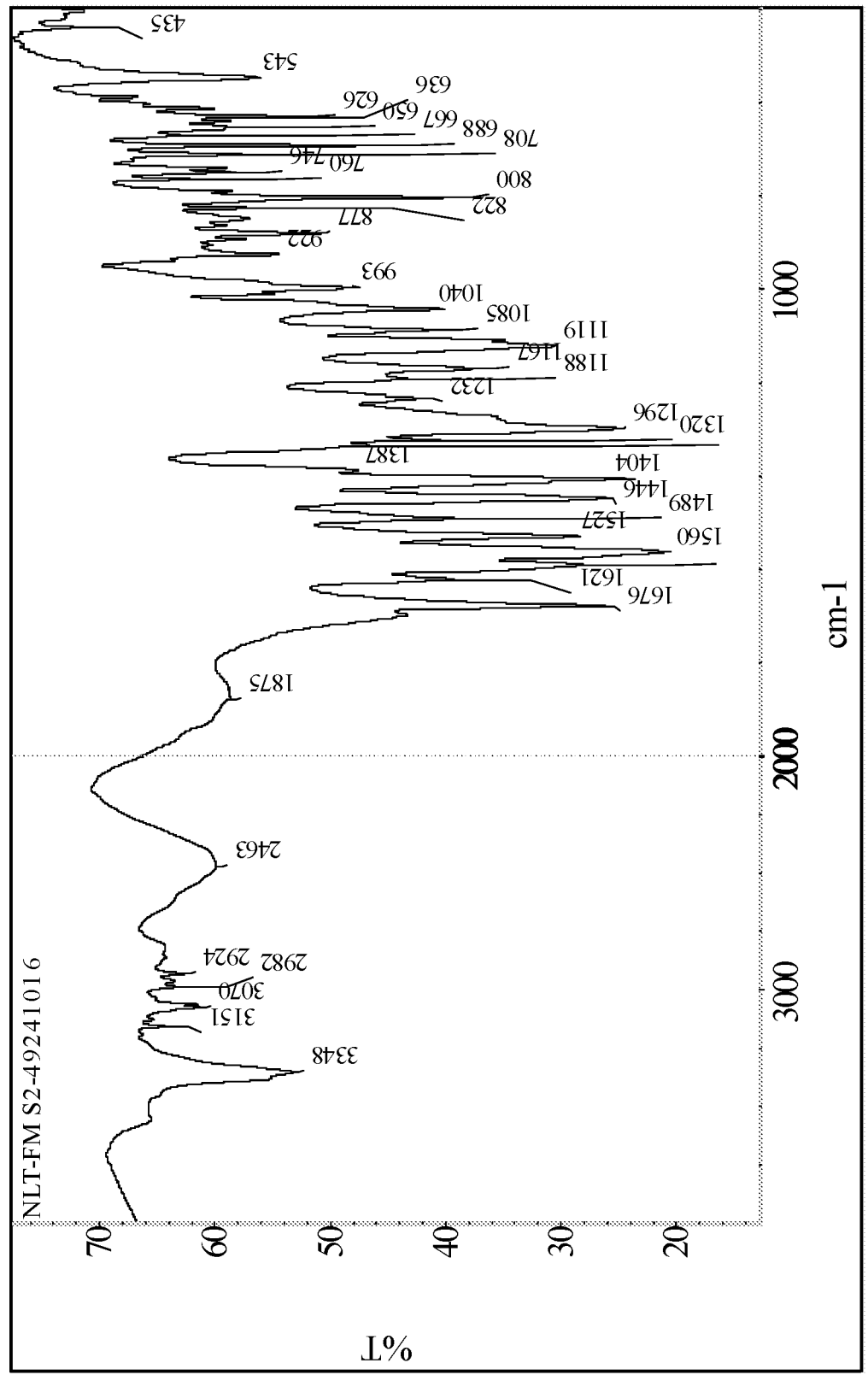
Figure 5. An FTIR spectrum of Nilotinib fumarate Form III

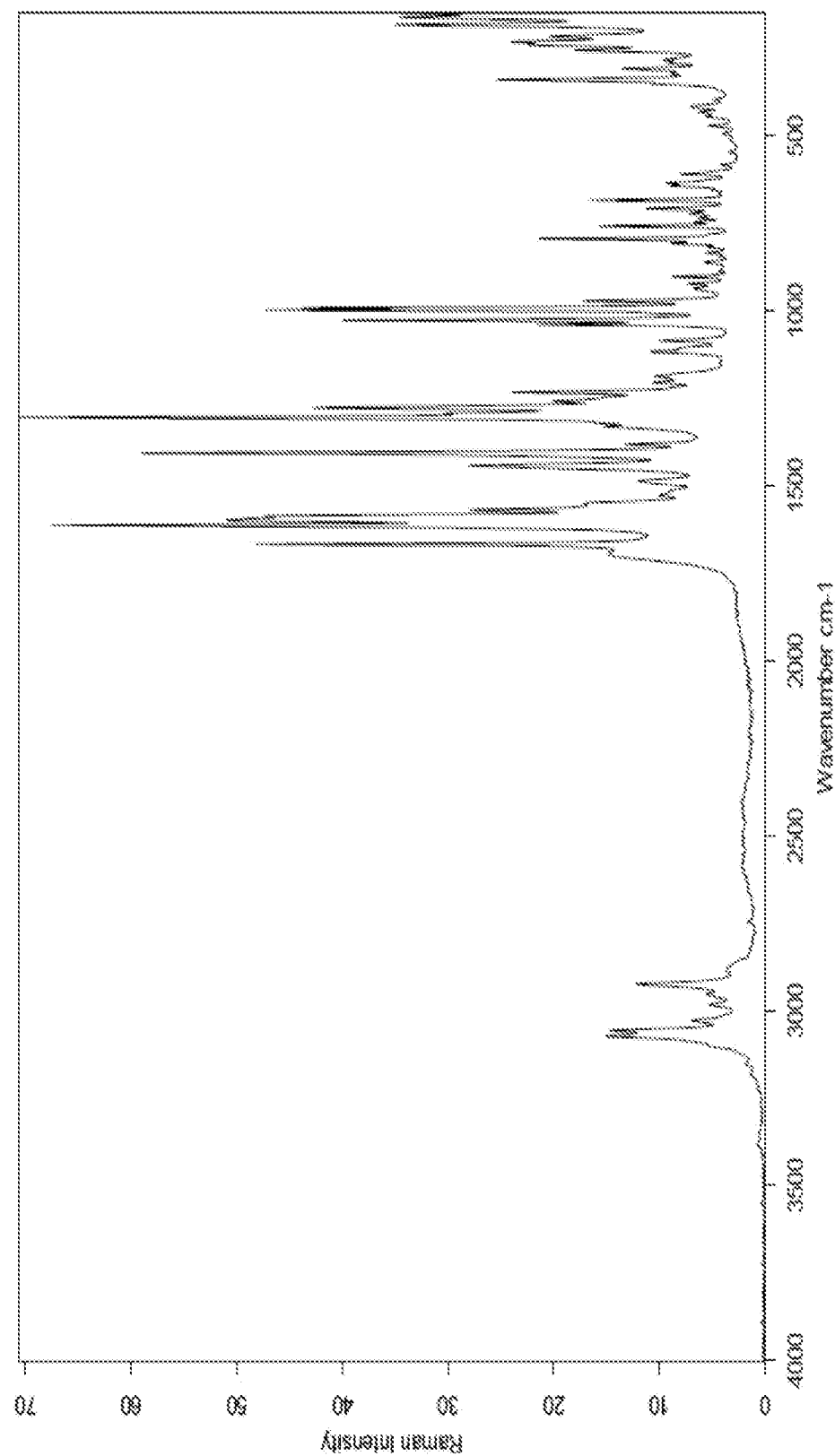
Figure 6. A Raman spectrum of Nilotinib fumarate Form III

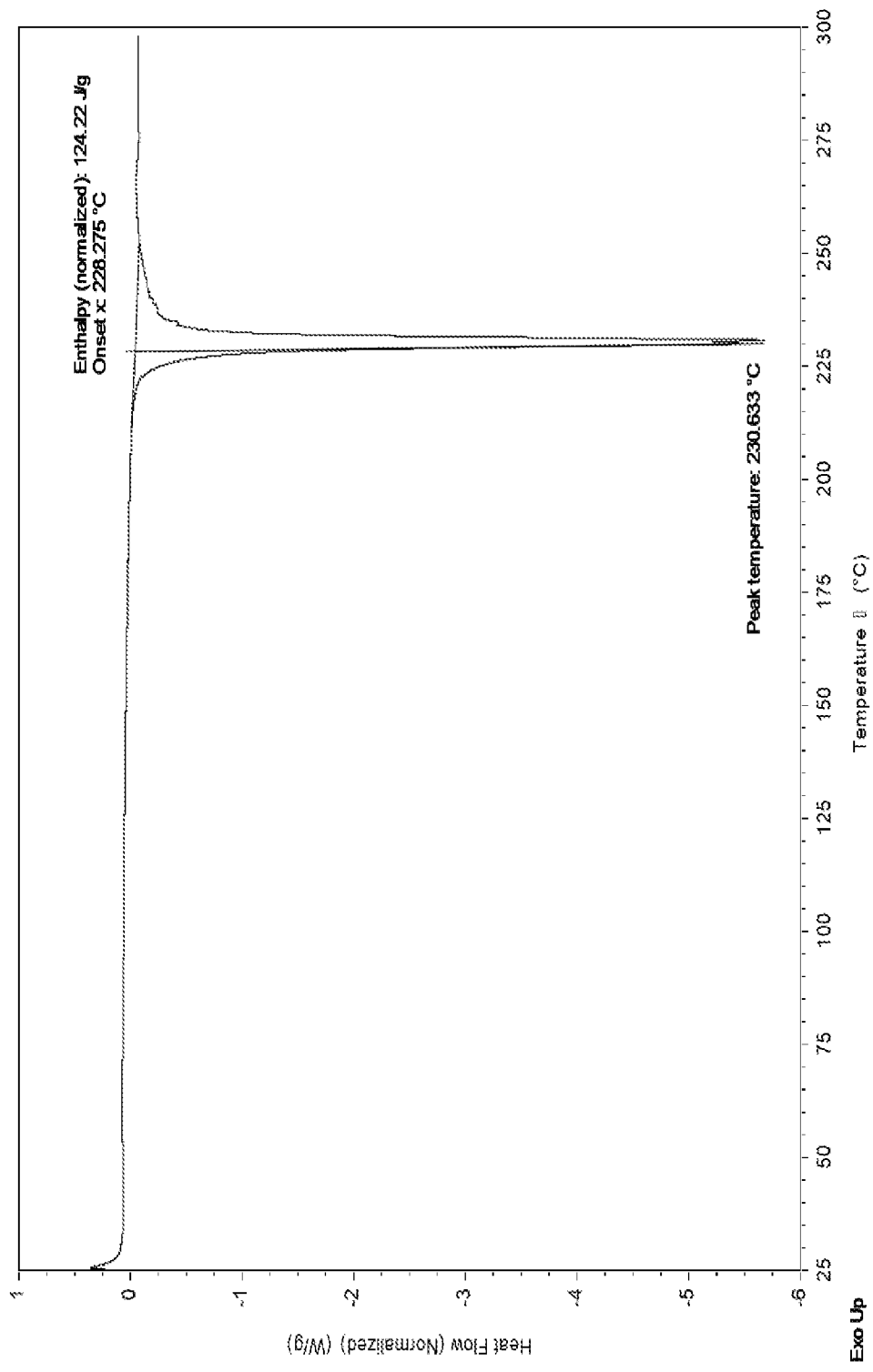
Figure 7. A DSC thermogram of Nilotinib fumarate Form III

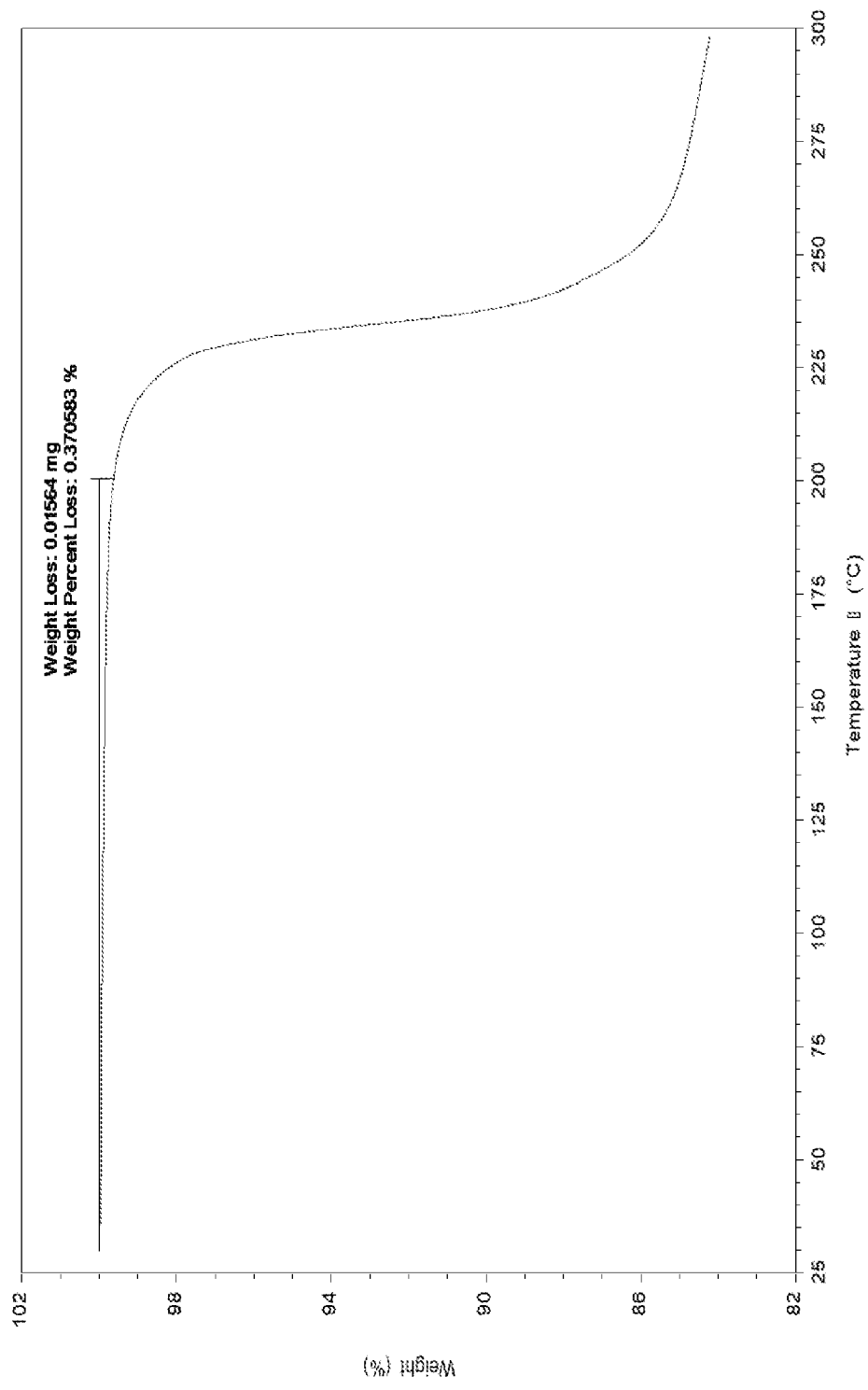
Figure 8. A TGA thermogram of Nilotinib fumarate Form III

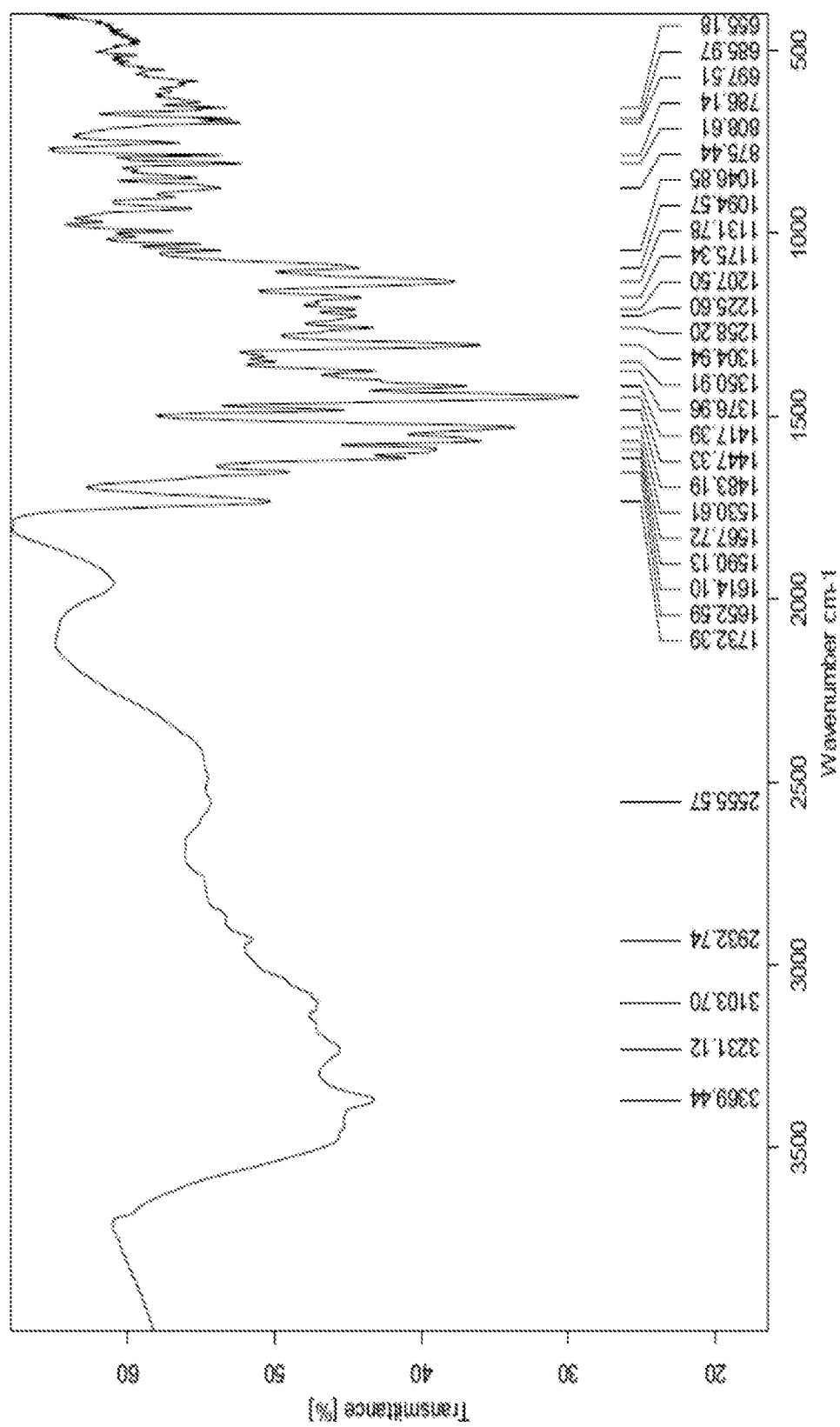
Figure 9. An FTIR spectrum of Nilotinib hydrochloride L-tartaric acid co-crystal Form I.

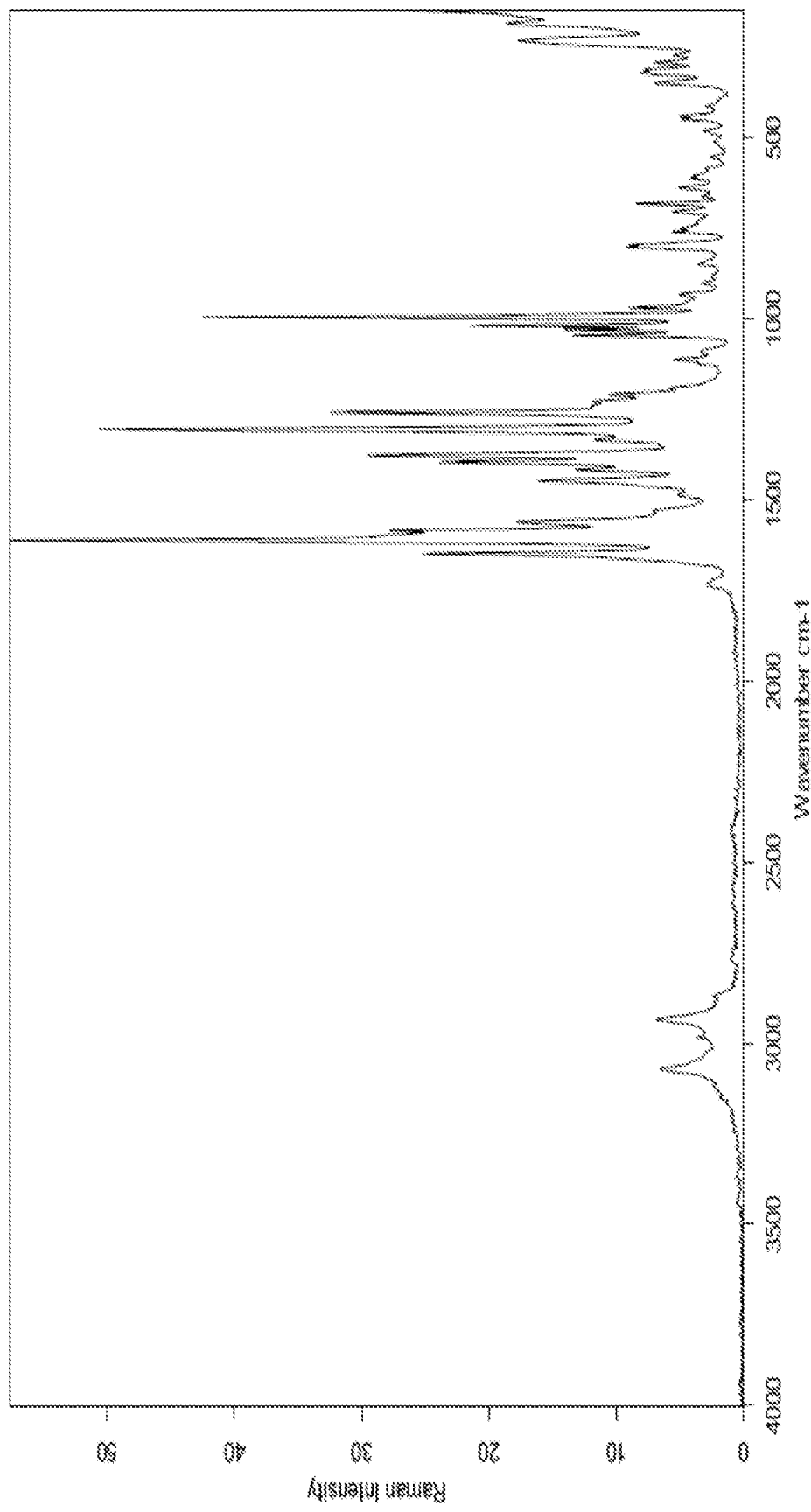
Figure 10. A Raman spectrum of Nilotinib hydrochloride L-tartaric acid co-crystal Form I.

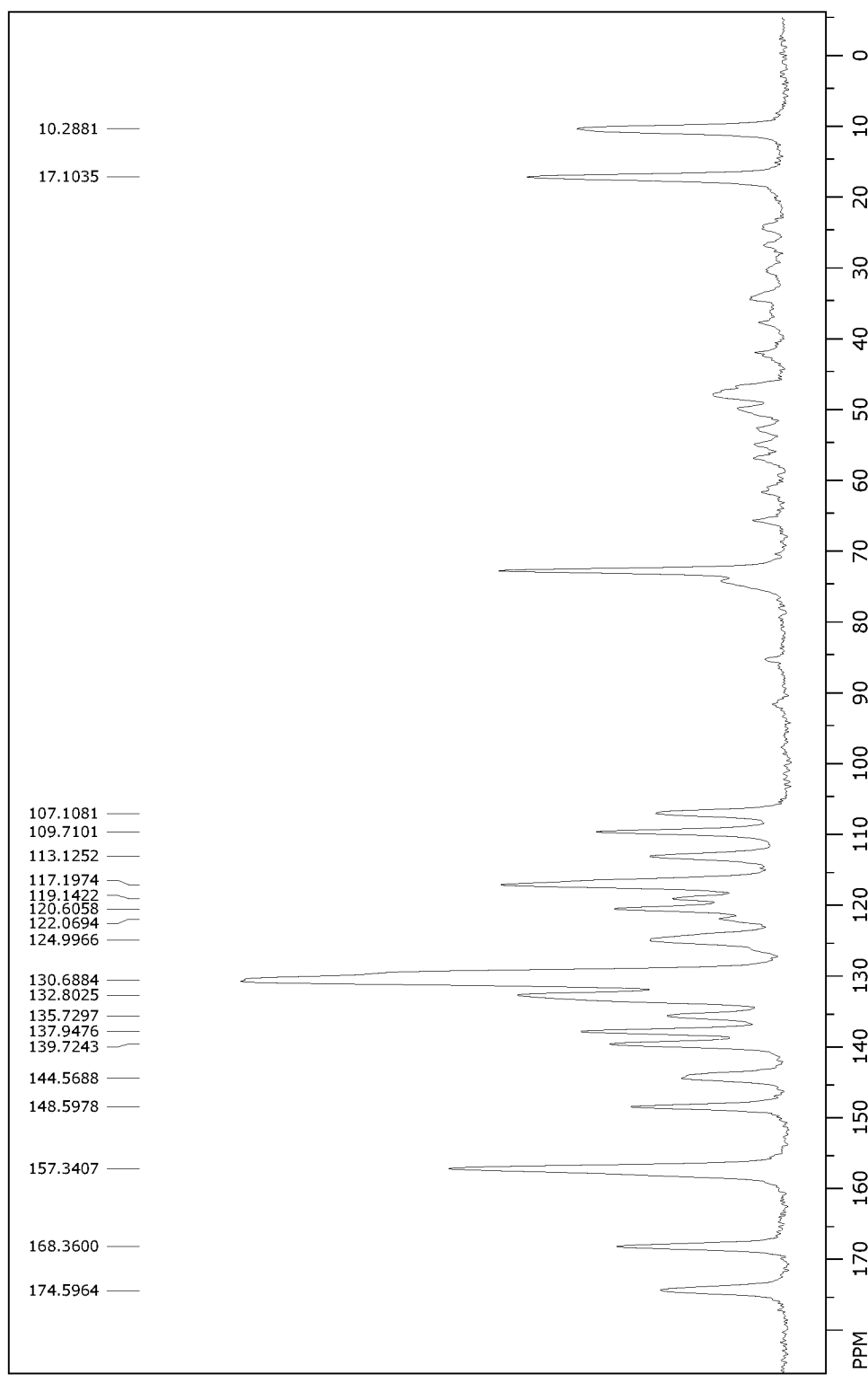
Figure 11. A solid state $^{13}$C NMR spectrum of Nilotinib hydrochloride L-tartaric acid co-crystal Form I.

SOLID STATE FORMS OF NILOTINIB SALTS

CROSS-REFERENCE TO RELATED APPLICATIONS

This application is the National Stage Application of International Patent Application No. PCT/US2017/022072, filed Mar. 13, 2017 which claims the benefit of U.S. Provisional Patent Application Nos. 62/307,841, filed Mar. 14, 2016 and 62/418,745, filed Nov. 7, 2016, the entireties of which are incorporated herein by reference.

TECHNICAL FIELD

The present disclosure relates to solid state forms of Nilotinib fumarate and Nilotinib hydrochloride L-tartaric acid co-crystals, processes for preparation thereof, pharmaceutical compositions thereof, and methods of use thereof.

BACKGROUND

Nilotinib, 4-methyl-N-[3-(4-methyl-1H-imidazol-1-yl)-5-(trifluoromethyl)phenyl]-3-[[4-(3-pyridinyl)-2-pyrimidinyl]amino]-benzamide, having the following formula:

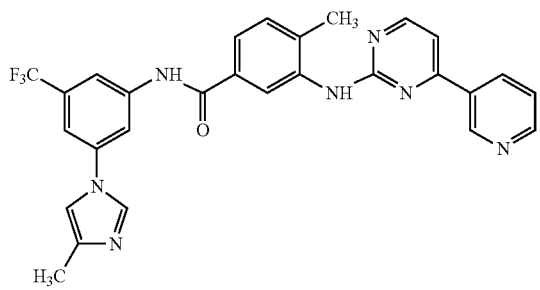 [SMILES: Cc1cn(-c2cc(NC(=O)c3ccc(C)c(Nc4nccc(-c5cccnc5)n4)c3)cc(C(F)(F)F)c2)cn1]

is a tyrosine kinase inhibitor used for the treatment of drug-resistant chronic myelogenous leukemia (CML), and in particular, for the treatment of chronic phase and accelerated phase Philadelphia chromosome positive CML in adult patients whose disease has progressed, or who cannot tolerate other therapies that include Imatinib. Nilotinib is administered as a hydrochloride salt in the form of capsules that are marketed in the USA and the EU under the name Tasigna®.

PCT publications WO 2007/015870 ("WO'870"), WO 2007/015871, WO2011/0163222 ("WO'222") and WO 2010/054056 ("WO'056") describe Nilotinib base and several Nilotinib salts, and crystalline and amorphous forms thereof. The crystalline forms exist in either solvate, anhydrous or hydrate forms. WO'222 describes crystalline forms I and II of Nilotinib Fumarate as well as several crystalline forms of Nilotinib Tartrate.

Polymorphism, the occurrence of different crystal forms, is a property of some molecules and molecular complexes. A single compound, like Nilotinib or a salt thereof, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}C$-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms (including solvated forms) of Nilotinib and salts thereof, for example of Nilotinib Fumarate.

SUMMARY

The present disclosure relates to solid state forms of Nilotinib Fumarate and Nilotinib hydrochloride L-tartaric acid co-crystals, to processes for preparation thereof, and to pharmaceutical compositions comprising these solid state forms.

The present disclosure also relates to uses of the solid state forms of Nilotinib fumarate and/or Nilotinib hydrochloride L-tartaric acid co-crystals of the present disclosure, for preparing Nilotinib, salts of Nilotinib, such as Nilotinib HCl, and solid state forms thereof, and other solid state forms of Nilotinib fumarate and/or Nilotinib hydrochloride L-tartaric acid co-crystals.

In another aspect, the present disclosure encompasses solid state forms of Nilotinib fumarate and/or Nilotinib hydrochloride L-tartaric acid co-crystals for use in the preparation of pharmaceutical compositions and/or formulations for use in medicine, preferably for the treatment of cancer, in particular, for the treatment of chronic myelogenous leukemia (CML).

The present disclosure also encompasses the uses of the solid state forms of Nilotinib fumarate and/or Nilotinib hydrochloride L-tartaric acid co-crystals for the preparation of pharmaceutical compositions and/or formulations.

The present disclosure further provides pharmaceutical compositions comprising any one of or a mixture of the solid state forms of Nilotinib Fumarate and/or Nilotinib hydrochloride L-tartaric acid co-crystals according to the present disclosure.

In yet another embodiment, the present disclosure encompasses pharmaceutical formulations comprising the solid state forms of Nilotinib fumarate and/or Nilotinib hydrochloride L-tartaric acid co-crystals, or of pharmaceutical compositions comprising the solid state forms of Nilotinib fumarate and/or Nilotinib hydrochloride L-tartaric acid co-crystals, and at least one pharmaceutically acceptable excipient.

The present disclosure further encompasses processes to prepare said pharmaceutical formulations of Nilotinib fumarate and/or of Nilotinib hydrochloride L-tartaric acid co-crystals comprising combining the state forms of Nilotinib fumarate and/or Nilotinib hydrochloride L-tartaric acid co-crystals, or pharmaceutical compositions comprising them, and at least one pharmaceutically acceptable excipient.

The solid state forms as defined herein as well as the pharmaceutical compositions or formulations of the solid state form of Nilotinib fumarate and/or forms of Nilotinib hydrochloride L-tartaric acid co-crystals can be used as medicaments, particularly for the treatment of cancer, especially CML, comprising administering a therapeutically effective amount of the solid state form of Nilotinib fumarate and/or forms of Nilotinib hydrochloride L-tartaric acid co-crystals of the present disclosure, or at least one of the above pharmaceutical compositions or formulations, to a subject suffering from cancer, or otherwise in need of the treatment.

The present disclosure also provides the solid state forms of Nilotinib fumarate and/or Nilotinib hydrochloride L-tartaric acid co-crystals of the present disclosure, or at least one of the above described pharmaceutical compositions or formulations, for use in medicine, preferably for treating cancer, in particular for treating CML.

The present disclosure also provides uses of the solid state forms of Nilotinib fumarate and/or Nilotinib hydrochloride L-tartaric acid co-crystals of the present disclosure, or at least one of the above pharmaceutical compositions or formulations for the manufacture of medicaments for treating cancer, in particular, for the treatment of CML.

BRIEF DESCRIPTION OF THE DRAWINGS

FIG. 1 shows an X-ray powder diffraction (XRPD) pattern of Nilotinib fumarate Form III.

FIG. 2 shows an XRPD pattern of Nilotinib hydrochloride L-tartaric acid co-crystal Form I.

FIG. 3 shows an XRPD pattern of Nilotinib hydrochloride L-tartaric acid co-crystal Form II.

FIG. 4 shows a solid state $^{13}$C-NMR spectrum of Nilotinib fumarate Form III.

FIG. 5 shows a Fourier-transform infrared (FTIR) spectrum of Nilotinib fumarate Form III.

FIG. 6 shows a Raman spectrum of Nilotinib fumarate Form III.

FIG. 7 shows a DSC thermogram of Nilotinib fumarate Form III.

FIG. 8 shows a TGA thermogram of Nilotinib fumarate Form III.

FIG. 9 shows an FTIR spectrum of Nilotinib hydrochloride L-tartaric acid co-crystal Form I.

FIG. 10 shows a Raman spectrum of Nilotinib hydrochloride L-tartaric acid co-crystal Form I.

FIG. 11 shows a solid state $^{13}$C NMR spectrum of Nilotinib hydrochloride L-tartaric acid co-crystal Form I.

DETAILED DESCRIPTION OF ILLUSTRATIVE EMBODIMENTS

The present disclosure relates to a solid state form of Nilotinib fumarate and to solid state forms of Nilotinib hydrochloride L-tartaric acid co-crystals, to processes for their preparation and to pharmaceutical compositions comprising any one of these solid state forms and/or combinations thereof. The disclosure also relates to the conversion of Nilotinib fumarate and/or Nilotinib hydrochloride L-tartaric acid co-crystals of the present disclosure to other solid state forms of Nilotinib fumarate and/or Nilotinib hydrochloride L-tartaric acid co-crystals, Nilotinib, other Nilotinib salts, such as Nilotinib HCl and solid state forms thereof.

The solid state forms according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Nilotinib or a Nilotinib salt, e.g., of Nilotinib fumarate or Nilotinib hydrochloride L-tartaric acid co-crystals referred to herein as being characterized by graphical data "as depicted in" a Figure will thus be understood to include any crystal forms of the Nilotinib fumarate, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% (w/w) of any other forms of the subject compound as measured, for example, by XRPD. Thus, solid state forms of Nilotinib fumarate described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of Nilotinib fumarate or Nilotinib hydrochloride L-tartaric acid co-crystals. Accordingly, in some embodiments of the disclosure, the described solid state forms of Nilotinib fumarate or Nilotinib hydrochloride L-tartaric acid co-crystals may contain from about 1% to about 20% (w/w), from about 5% to about 20% (w/w), or from about 5% to about 10% (w/w) of one or more other solid state forms of the same Nilotinib fumarate or Nilotinib hydrochloride L-tartaric acid co-crystals.

As used herein, unless stated otherwise, XRPD peaks reported herein are measured using CuK$_\alpha$ radiation, λ=1.54184 Å. Preferably, XRPD peaks reported herein are measured using CuK$_\alpha$ radiation, λ=1.54184 Å, at a temperature of 25±3° C. Alternatively, if an instrument with a different wavelength is used, for example, when using high resolution XRD method, such as synchrotron, the data may be corrected to wavelength of 1.54184 respectively.

As used herein, the term "isolated" in reference to solid state forms of Nilotinib fumarate or Nilotinib hydrochloride L-tartaric acid co-crystals of the present disclosure corresponds to solid state form of Nilotinib fumarate or Nilotinib hydrochloride L-tartaric acid co-crystal that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, and the like.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, and the like.

As used herein, and unless stated otherwise, the term "anhydrous" in relation to crystalline Nilotinib fumarate or Nilotinib hydrochloride L-tartaric acid co-crystals relates to crystalline Nilotinib fumarate or Nilotinib hydrochloride L-tartaric acid co-crystals, which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein the term non-hygroscopic in relation to the crystalline forms of the present disclosure refers to less than about 1.0% (w/w) absorption of water at about 25° C. and about 80% relative humidity (RH), by the crystalline forms of the present disclosure as determined for example by TGA. Water can be for example atmospheric water.

As used herein, the term "reduced pressure" refers to a pressure of about 10 mbar to about 50 mbar.

As used herein, and unless indicated otherwise, the term "thermo-dynamical stability" in relation to solid state forms of the present disclosure refers to resistance of the solid state form to polymorphic conversion under certain conditions, for example, heating, melting or dissolving. In some embodiments, the term refers to less than about 20% (w/w), about 10% (w/w), about 5% (w/w), about 1% (w/w), about 0.5% (w/w), or about 0% (w/w) conversion of the solid state forms of the present disclosure to any other solid state form of Nilotinib fumarate or Nilotinib hydrochloride L-tartaric acid co-crystals as measured by XRPD. In some embodiments, the conversion is about 1% (w/w) to about 20% (w/w), about 1% (w/w) to about 10% (w/w) or about 1% (w/w) to about 5% (w/w).

As used herein Nilotinib HCl Form T17 refers to the crystalline form provided in WO'056, which may be characterized by an X-ray powder diffraction pattern having peaks at 5.7, 9.8, 15.0, 15.8 and 17.3 degrees two theta ±0.2 degrees two theta. Nilotinib HCl Form T17 may be further characterized by x-ray powder diffraction pattern having additional peaks at about 7.5, 11.4, 18.6, 19.6 and 20.7 degrees two theta ±0.2 degrees two theta or at about 7.6, 11.4, 18.7, 19.7 and 20.7 degrees two theta ±0.2 degrees two theta.

The present disclosure comprises a crystalline form of Nilotinib fumarate designated as Form III. The crystalline Form III of Nilotinib fumarate can be characterized by data selected from one or more of the following: an XRPD pattern having peaks at 5.5, 7.0, 11.0, 13.4 and 15.8 degrees two theta ±0.2 degrees two theta; an XRPD pattern substantially as depicted in FIG. 1; a solid state $^{13}$C NMR spectrum having characteristic peaks at 168.9, 159.1, 135.4 and 114.7±0.2 ppm; a solid state $^{13}$C NMR spectrum substantially as depicted in FIG. 4; a solid state $^{13}$C NMR spectrum having the following chemical shift absolute differences from a peak at 119.0 ppm ±1 ppm of +49.9, +40.1, +16.4 and −4.3 ppm ±0.1 ppm; a solid state $^{13}$C NMR spectrum having chemical shift difference from a peak at 119.0 ppm ±1 ppm of +40.1 ppm ±0.1 ppm; and combinations of these data.

Crystalline Form III of Nilotinib fumarate may be further characterized by data selected from one or more of the following: an XRPD pattern having peaks at 5.5, 7.0, 11.0, 13.4 and 15.8 degrees two theta ±0.2 degrees two theta, and also having one, two, three, four, five, six or seven additional peaks selected from 14.0, 14.9, 16.3, 20.4, 20.5, 20.9 and 25.3 degrees two theta ±0.2 degrees two theta; an FTIR spectrum having peaks at 3348, 1676, 1560, 1404 and 1296±4 cm$^{-1}$; an FTIR spectrum substantially as depicted in FIG. 5; a Raman spectrum having peaks at 1668, 1614, 1407 and 1306±4 cm$^{-1}$; a Raman spectrum substantially as depicted in FIG. 6; DSC endothermic peak of melting at about 228° C. (onset); a DSC thermogram substantially as depicted in FIG. 7; a TGA thermogram substantially as depicted in FIG. 8; and combinations of these data.

Crystalline Form III of Nilotinib fumarate may be further characterized by XRPD pattern comprising the following peaks ±0.2 degrees two theta):

| XRPD peaks (degrees two theta ± 0.2 degrees two theta) |
|---|
| 5.5 |
| 7.0 |
| 7.6 |
| 10.2 |
| 11.0 |
| 13.4 |
| 14.0 |
| 14.9 |
| 15.1 |
| 15.8 |
| 16.3 |
| 16.6 |
| 17.1 |
| 17.4 |
| 18.5 |
| 19.3 |
| 19.6 |
| 19.9 |
| 20.4 |
| 20.5 |
| 20.9 |
| 21.2 |
| 21.8 |
| 22.6 |
| 23.0 |
| 23.5 |
| 24.0 |
| 24.6 |
| 24.8 |
| 25.3 |
| 26.3 |
| 26.5 |
| 27.1 |
| 27.6 |
| 27.9 |
| 29.2 |
| 29.4 |
| 34.8 |
| 37.8 |
| 38.1 |

Crystalline Form III of Nilotinib fumarate may be further characterized by a solid state $^{13}$C NMR spectrum having the following peaks at: 10.9, 19.3, 107.1, 108.5, 110.7, 111.6, 114.7, 119.0, 123.0, 125.2, 128.2, 128.8, 130.1, 132.9, 134.7, 135.4, 136.2, 137.4, 141.2, 145.1, 147.7, 159.1, 163.9, 168.0, 168.9 ppm ±0.2 ppm).

Crystalline Form III of Nilotinib fumarate may be further characterized by FTIR spectrum comprising the following peaks: 3348, 3151, 3056, 3071, 2924, 2463, 1698, 1676, 1621, 1588, 1560, 1527, 1489, 1446, 1404, 1320, 1296, 1231, 1188, 1167, 1119, 1085, 1040, 993, 922, 877, 846, 822, 800, 760, 746, 737, 708, 688, 649, 626, 609, 585 and 543 cm$^{-1}$±1 cm$^{-1}$.

Crystalline Form III of Nilotinib fumarate may be further characterized by Raman spectrum comprising the following peaks: 3073, 2925, 1668, 1614, 1600, 1570, 1487, 1443, 1407, 1382, 1306, 1278, 1234, 1118, 1086, 1040, 1028, 999, 992, 973, 903, 795, 759, 709, 685, 636 and 610 cm$^{-1}$±4 cm$^{-1}$.

Form III of Nilotinib fumarate may be an anhydrous form.

Crystalline Form III of Nilotinib fumarate may be characterized by each of the above characteristics alone and/or by all possible combinations. For example, crystalline Form III of Nilotinib fumarate may be characterized by a PXRD pattern as depicted in FIG. 1 and also by an FTIR spectrum having peaks at 3348, 1676, 1560, 1404 and 1296±4 cm$^{-1}$.

Form III of Nilotinib fumarate may have advantageous properties selected from at least one of: chemical or polymorphic purity, flowability, solubility, wettability, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, or bulk density. Particularly, crystalline Form III of Nilotinib fumarate of the present disclosure is chemically and polymorphically stable, as was confirmed for example in long term stability conditions at 5° C. and accelerated stability conditions at 25° C./60% RH with desiccant. In addition, when compared to forms I and II of Nilotinib fumarate described in WO'222, Form III of Nilotinib fumarate of the present disclosure has higher crystallinity, and is thermodynamically more stable. A stable polymorph (which does not convert to other forms or a mixture of forms), facilitates the handling and formulation of the API, and thus enables a reliable and reproducible formulation manufacturing processing. As a result the formulation process enables readily reproducible formulations in terms of solubility, bioavailability, etc. In addition Form III can be obtained from a number of pharmaceutically acceptable solvents, while forms I and II are obtained from 2,2,2-trifluoroethanol (TFE), which is a toxic solvent. Being able to manufacture Form III of Nilotinib fumarate from a less toxic solvent system offers a distinct advantage over Forms I and II of WO'222. Moreover, for solvated forms of a crystalline compound (such as Forms I and II of WO'222) there is always the possibility that some of the solvent is lost during the drying and processing steps, which is generally disadvantageous in view of the potential problems with the defined weight of the material. In contrast, Form III of Nilotinib fumarate of the present disclosure is an anhydrous form and is therefore not at risk to loose solvent during the manufacturing and/or drying steps.

In another embodiment, the present disclosure comprises a co-crystal of Nilotinib hydrochloride L-tartaric acid designated as Form I. The co-crystal Form I of Nilotinib hydrochloride L-tartaric acid can be characterized by data selected from one or more of the following: an XRPD pattern having peaks at 5.9, 8.1, 14.2, 14.6 and 19.7 degrees two theta ±0.2 degrees two theta; an XRPD pattern substantially as depicted in FIG. 2; a solid state $^{13}$C NMR spectrum having characteristic peaks at 174.5, 168.4, 157.3 and 130.8±0.2 ppm; a solid state $^{13}$C NMR spectrum substantially as depicted in FIG. 11; a solid state $^{13}$C NMR spectrum having the following chemical shift absolute differences from a peak at 117.2 ppm ±1 ppm of 57.3, 51.2, 40.1 and 13.6 ppm ±0.1 ppm, respectively; a solid state $^{13}$C NMR spectrum having chemical shift difference from a peak at 117.2 ppm ±1 ppm of 40.1 ppm ±0.1 ppm; and combinations of these data.

Co-crystal Form I of Nilotinib hydrochloride L-tartaric acid may be further characterized by data selected from one or more of the following: an XRPD pattern having peaks at 5.9, 8.1, 14.2, 14.6 and 19.7 degrees two theta ±0.2 degrees two theta; and also having one, two, three, four or five additional peaks selected from 11.1, 11.8, 17.1, 18.6 and 26.2 degrees two theta ±0.2 degrees two theta; an FTIR spectrum having peaks at 3369, 1732, 1653, 1531 and 1447±4; an FTIR spectrum substantially as depicted in FIG. 9; a Raman spectrum having peaks at 1649, 1613, 1447 and 1306±4 cm$^{-1}$; a Raman spectrum substantially as depicted in FIG. 10; and combinations of these data.

Crystalline Form I of Nilotinib hydrochloride L-tartaric acid may be further characterized by XRPD pattern comprising the following peaks ±0.2 degrees two theta):

| XRPD peaks (degrees two theta ± 0.2 degrees two theta) |
|---|
| 5.9 |
| 8.1 |
| 8.6 |
| 8.8 |
| 10.4 |
| 11.1 |
| 11.8 |
| 12.9 |
| 13.6 |
| 14.2 |
| 14.6 |
| 16.3 |
| 17.1 |
| 17.5 |
| 17.7 |
| 17.9 |
| 18.2 |
| 18.6 |
| 19.7 |
| 20.5 |
| 21.0 |
| 21.2 |
| 22.0 |
| 22.3 |
| 22.6 |
| 23.1 |
| 23.4 |
| 23.6 |
| 24.0 |
| 24.4 |
| 24.8 |
| 25.3 |
| 25.8 |
| 26.2 |
| 26.9 |
| 27.2 |
| 27.5 |
| 27.9 |
| 28.9 |
| 29.3 |
| 29.8 |
| 30.6 |
| 31.5 |
| 31.9 |
| 32.6 |
| 33.2 |
| 33.5 |
| 34.4 |
| 35.4 |
| 36.0 |
| 36.4 |
| 37.0 |
| 37.6 |
| 38.3 |
| 39.4 |

Crystalline Form I of Nilotinib hydrochloride L-tartaric acid may be further characterized by a solid state $^{13}$C NMR spectrum having the following peaks at: 10.3, 17.1, 107.1, 109.7, 113.1, 117.2, 119.1, 120.6, 122.0, 125.0, 130.8, 132.8, 135.7, 138.0, 144.5, 148.6, 157.3, 168.4 and 174.5 ppm ±0.2 ppm.

Crystalline Form I of Nilotinib hydrochloride L-tartaric acid may be further characterized by FTIR spectrum comprising the following peaks: 3369, 3231, 3104, 2933, 2556, 1732, 1653, 1614, 1590, 1568, 1531, 1483, 1447, 1417, 1377, 1351, 1305, 1258, 1226, 1208, 1175, 1132, 1095, 1047, 875, 809, 786, 698, 686 and 655 cm$^{-1}$±1 cm$^{-1}$.

Crystalline Form I of Nilotinib hydrochloride L-tartaric acid may be further characterized by Raman spectrum comprising the following peaks: 3071, 2935, 1735, 1649, 1613, 1586, 1561, 1447, 1418, 1396, 1377, 1335, 1306, 1259, 1210, 1113, 1046, 1031, 1020, 997, 970, 933, 850, 803, 761, 704, 682, 638 and 613 cm$^{-1}$±4 cm$^{-1}$.

The ratio between Nilotinib hydrochloride and L-tartaric acid in co-crystal form I is about 2:1, as was determined by NMR (see Example 4).

Crystalline Form I of Nilotinib hydrochloride L-tartaric acid may be a solvate such as ethanolate or methanolate or a hydrate. Preferably, Crystalline Form I of Nilotinib hydrochloride L-tartaric acid is a hydrate.

Form I of Nilotinib hydrochloride L-tartaric acid may be characterized by each of the above characteristics alone and/or by all possible combinations. For example, crystalline Form I of Nilotinib hydrochloride L-tartaric acid may be characterized by a PXRD pattern as depicted in FIG. 2 and also by an FTIR spectrum having peaks at 3369, 1732, 1653, 1531 and 1447±4 cm$^{-1}$.

Form I of Nilotinib hydrochloride L-tartaric acid may be characterized by each of the above characteristics alone and/or by all possible combinations. For example, crystalline Form I of Nilotinib hydrochloride L-tartaric acid may be characterized by a PXRD pattern as depicted in FIG. 2 and also by an FTIR spectrum having peaks at 3369, 1732, 1653, 1531 and 1447±4 cm$^{-1}$.

Form I of Nilotinib hydrochloride L-tartaric acid may have advantageous properties selected from at least one of: chemical or polymorphic purity, flowability, solubility, wettability, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, or bulk density. Particularly, crystalline Form I of Nilotinib hydrochloride L-tartaric acid of the present disclosure has high bulk density, as measured by Ph. Eur. 2.9.34/USP <616> method (GMP000582/5), compared for example to form B of Nilotinib HCl described in WO'870. A material having higher bulk density typically exhibits better filterability and flowability.

Form I of Nilotinib hydrochloride L-tartaric acid may have advantageous properties selected from at least one of: chemical or polymorphic purity, flowability, solubility, wettability, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, or bulk density. Particularly, crystalline Form I of Nilotinib hydrochloride L-tartaric acid of the present disclosure has high bulk density, as measured by Ph. Eur. 2.9.34/USP <616> method (GMP000582/5), compared for example to form B of Nilotinib HCl described in WO'870. A material having higher bulk density typically exhibits better filterability and flowability.

Good filterability is a prerequisite for enabling the production of the API on an industrial scale. A good flowability of a powder is particularly important in the high-volume formulation of the API into solid dosage forms, which necessitates rapid, uniform and consistent filling of cavities such as capsules, or tablet presses. Poor flow characteristics cause slow and nonuniform press feeding and difficulties in ensuring a consistent, reproducible fill of the cavities.

Therefore, Form I of Nilotinib hydrochloride L-tartaric acid of the present disclosure has favorable technological (physical and mechanical) properties, which offers advantages during handling and processing, e.g., in tablet formulation processes.

In yet another embodiment, the present disclosure comprises a co-crystal of Nilotinib hydrochloride L-tartaric acid designated as Form II. The co-crystal Form II of Nilotinib hydrochloride L-tartaric acid can be characterized by data selected from one or more of the following: an XRPD pattern having peaks at 4.2, 7.2, 8.4, 11.7 and 12.6 degrees two theta ±0.2 degrees two theta; an XRPD pattern substantially as depicted in FIG. 3; or combinations of these data.

Co-crystal Form II of Nilotinib hydrochloride L-tartaric acid may be further characterized by an XRPD pattern having peaks at 4.2, 7.2, 8.4, 11.7 and 12.6 degrees two theta ±0.2 degrees two theta; and also having one, two, three, four or five additional peaks selected from 14.3, 17.6, 23.4, 24.6 and 25.4 degrees two theta ±0.2 degrees two theta.

The present disclosure also provides the use of the solid state forms of Nilotinib fumarate and/or or Nilotinib hydrochloride L-tartaric acid co-crystals for preparing other solid state forms of Nilotinib fumarate or Nilotinib hydrochloride L-tartaric acid co-crystals, Nilotinib, other Nilotinib salts, such as Nilotinib HCl, and solid state forms thereof.

The present disclosure further encompasses processes for preparing Nilotinib or solid state forms thereof. The process for preparing Nilotinib or solid state forms thereof comprises preparing the Nilotinib fumarate solid state form or any one of the Nilotinib hydrochloride L-tartaric acid co-crystals, according to the present disclosure, and converting it to Nilotinib or solid state forms thereof. The conversion can be done, for example, by reacting the solid state form of Nilotinib fumarate or Nilotinib hydrochloride L-tartaric acid co-crystals described herein with a suitable base to obtain Nilotinib.

The present disclosure further encompasses processes for preparing other Nilotinib salts, such as Nilotinib HCl, or solid state forms thereof. The process comprises preparing the solid state form of Nilotinib fumarate or Nilotinib hydrochloride L-tartaric acid co-crystals of the present disclosure, and converting it to other Nilotinib salt. The conversion can be done, for example, by a process comprising converting Nilotinib fumarate or Nilotinib hydrochloride L-tartaric acid co-crystals to Nilotinib according to the above procedure and reacting the obtained Nilotinib with an appropriate acid to obtain the corresponding acid addition salt. Alternatively, the Nilotinib salt can be prepared by salt switching, i.e., reacting Nilotinib fumarate, Nilotinib hydrochloride L-tartaric acid co-crystals or any of the solid state forms thereof, with an acid, having a $pK_a$ which is lower than the $pK_a$ of fumaric acid or hydrochloric acid, respectively.

In another embodiment, the present disclosure encompasses the use of the above described solid state form of Nilotinib fumarate or forms of Nilotinib hydrochloride L-tartaric acid co-crystals for the preparation of pharmaceutical compositions and/or formulations.

The present disclosure further provides pharmaceutical compositions comprising the solid state form of Nilotinib fumarate or forms of Nilotinib hydrochloride L-tartaric acid co-crystals according to the present disclosure.

In yet another embodiment, the present disclosure encompasses pharmaceutical formulations comprising the above described solid state form of Nilotinib fumarate or forms of Nilotinib hydrochloride L-tartaric acid co-crystals and/or combinations thereof, or a pharmaceutical composition as described above, and at least one pharmaceutically acceptable excipient.

The present disclosure moreover encompasses processes to prepare said formulations comprising combining the above described solid state form of Nilotinib fumarate or forms of Nilotinib hydrochloride L-tartaric acid co-crystals and/or combinations thereof and at least one pharmaceutically acceptable excipient.

In another embodiment, the present disclosure encompasses the above described solid state form of Nilotinib fumarate or forms of Nilotinib hydrochloride L-tartaric acid co-crystals for use in medicine, preferably for the treatment of cancer, for example, the treatment of CML.

The present disclosure also provides methods of treating cancer, in particular CML, comprising administering a therapeutically effective amount of the solid state form of Nilotinib fumarate or forms of Nilotinib hydrochloride L-tartaric acid co-crystals of the present disclosure, or at least one of the above described pharmaceutical compositions or formulations, to a subject suffering from cancer, or otherwise in need of the treatment.

The present disclosure also provides the use of the solid state form of Nilotinib fumarate or forms of Nilotinib hydrochloride L-tartaric acid co-crystals of the present disclosure, or at least one of the above described pharmaceutical compositions or formulations for the manufacture of a medicament for treating cancer, in particular for treating CML.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-Ray Powder Diffraction Pattern ("XRPD") Method:

The sample, after being powdered in a mortar and pestle, is applied directly on a silicon plate holder. The X-ray powder diffraction pattern was measured with a Philips X'Pert PRO X-ray powder diffractometer, equipped with Cu irradiation source=1.54184 Å (Angstrom), and an X'Celerator (2.022° 2θ) detector. Scanning parameters: angle range: 3-40°, step size 0.0167, time per step 37 s, continuous scan. The described peak positions were determined using silicon powder as an internal standard in an admixture with the sample measured.

$^1$H-NMR Method:

NMR spectrum was recorded on a Bruker Avance DRX 500 spectrometer using standard Bruker pulse sequences, at 25° C. in DMSO-$d_6$ as a solvent and TMS as the internal standard.

Differential Scanning Calorimetry ("DSC")

DSC analysis was performed on Q1000 MDSC (TA instruments) with heating rate of 10° C./min, under nitrogen flow of 50 ml/min. A hermetic aluminium, closed pan with hole was used, and the sample mass was about 1-5 mg.

Thermogravimetric Analysis ("TGA")

TGA analysis was performed on instruments Mettler Toledo TG-DSC 1 and Mettler Toledo TGA/SDTA 851$^e$ with a heating rate of 10° C./min and under nitrogen flow of 30 mL/min. Standard aluminum open pan was used, sample mass was 1-10 mg.

Fourier Transform Infrared Spectroscopy ("FTIR")

Sample (1-2 mg) was triturated with 200-300 mg of dry potassium bromide and mixture was compressed into a pellet with a pressure of 700 MPa. The spectrum of the sample was recorded over the range 4000 to 400 cm$^{-1}$, with resolution of 2 cm$^{-1}$ and 16 scans. For background spectrum, air was used (empty sample compartment). Analysis was performed on Nicolet 6700.

FT-Raman Spectroscopy ("Raman")

Raman spectra were acquired on a Nicolet 6700 interferometer equipped with an NXR FT-Raman module. Nd-YAG laser (1064 nm, 500 mW) was used to excite the sample. The spectrometer utilizes a CaF$_2$ beamsplitter and a liquid nitrogen cooled Ge detector. The spectra were recorded at a resolution of 4 cm$^{-1}$.

Solid State Nuclear Magnetic Resonance ("ssNMR")

Solid-state $^{13}$C NMR spectra were recorded with variable amplitude cross polarization, magic angle spinning and high power proton decoupling using a BRUKER Avance II+ spectrometer operating at 125 MHz and ambient temperature (about 25° C.—not controlled). A probe using 4 mm o.d. zirconia rotors was employed. The operation conditions were: contact time: 2 ms; recycle delay: 2 s 1024 scans; spin rate of 11 kHz. Chemical shifts were referenced via a replacement sample of glycine (carboxyl carbon chemical shift assigned as 176.03 ppm relative to the signal of tetramethylsilane).

EXAMPLES

Nilotinib base can be prepared according to the process described in WO'222.

Nilotinib hydrochloride can be prepared according to the process described in WO'056.

Example 1: Preparation of Nilotinib Fumarate Form III

Nilotinib base (1.0 g; 1.84 mmol) was suspended in ethanol, 96% (50 mL) and acetic acid (1 mL). Fumaric acid (0.25 g; 2.13 mmol) was added. The reaction mixture was heated to about 80° C. and the obtained solution is filtered. The filtrate was cooled to 20-25° C. The precipitate was filtered, washed with ethanol, abs. to obtain 0.57 g (48.0%) of Nilotinib fumarate Form III, as was confirmed by XRPD.

Example 2. Preparation of Nilotinib Fumarate Form III

Nilotinib base (1.0 g; 1.84 mmol) was suspended in 1-butanol (32 mL) and methanol (8 mL). Fumaric acid (0.25 g; 2.13 mmol) was added. The reaction mixture was heated to about 85° C. and the obtained solution was filtered. The filtrate was cooled to 0-5° C. and stirred for about 2 h. The precipitate was filtered, washed with 1-butanol/methanol 4:1 (5 mL) and dried in a vacuum oven at 70° C./20 mbar/10 h to obtain 1.02 g (85.8%) of Nilotinib fumarate Form III, as was confirmed by XRPD.

Example 3. Preparation of Nilotinib Fumarate Form III

Nilotinib base (10.0 g; 18.4 mmol) was suspended in 1-butanol (400 mL) and ethanol, abs. (100 mL). Fumaric acid (2.5 g; 21.3 mmol) was added to the suspension. The reaction mixture was heated to 90-95° C. and the obtained solution was filtered. The filtrate was cooled to 45° C. and stirred for about 2 h, then cooled to 20° C. and stirred for about 18 h. The precipitate was filtered, washed with 1-butanol/ethanol, abs.=1:4 (50 mL) and ethanol, abs. (10 mL). The obtained solid was dried in a vacuum oven at 70° C./20 mbar/10 h to obtain 11.13 g (93.6%) of Nilotinib fumarate Form III, as characterized by XRPD (FIG. 1).

Example 4. Preparation of Nilotinib Hydrochloride L-Tartaric Acid Co-Crystal Form I A suspension of Nilotinib hydrochloride (1.0 g) and L-tartaric acid (0.5 g) in methanol:isopropanol 1:1 (20 mL) was dissolved at 70-75° C. The obtained solution was cooled to room temperature (RT) and stirred for about 3 days. The obtained precipitate was filtered and washed with methanol: isopropanol 1:1. The solid was heated (50 mg) to 130° C. (10° C./min) under nitrogen flow (10 mL/min) to provide Nilotinib hydrochloride L-tartaric acid co-crystal Form I, as characterized by XRPD (FIG. 1).

Example 5. Preparation of Nilotinib Hydrochloride L-Tartaric Acid Co-Crystal Form I A suspension of Nilotinib base (5.0 g) in ethanol abs. (150 mL) was heated to reflux. An ethanolic solution of hydrochloric acid (1.25M; 9 mL) was added drop wise to the suspension to provide a solution. The obtained solution was filtered and the filtrate heated to 70-75° C. A solution of L-tartaric acid (1.55 g) in ethanol abs. (15 mL) was added to the reaction mixture. The resulting solution was cooled to room temperature (RT) and stirred for about 24 h. The suspension was filtered and the filtrate stirred at RT for 2 days. The obtained precipitate was filtered and dried in a vacuum oven at about 50° C./20 mbar to provide Nilotinib hydrochloride L-tartaric acid co-crystal Form I, as was confirmed by XRPD.

Example 6. Preparation of Nilotinib Hydrochloride L-Tartaric Acid Co-Crystal Form I Nilotinib hydrochloride Form T17 (500 mg) and L-tartaric acid (172 mg) were mixed to obtain a homogenous mixture. 300 mg of mixture was placed in a ball mill (agate, 25 mL) and one drop of ethanol abs. was added. The mixture was milled for 2.5 h at 500 rpm with 3 agate balls to provide Nilotinib hydrochloride L-tartaric acid co-crystal Form I, as was confirmed by XRPD.

Example 7. Preparation of Nilotinib Hydrochloride L-Tartaric Acid Co-Crystal Form I A suspension of Nilotinib hydrochloride Form T17 (56.6 mg) and L-tartaric acid (15.0 mg) in ethanol abs. (1 mL) was stirred for 36 hours at 35° C. The resulting suspension was filtered and the obtained solid dried under vacuum at RT to provide Nilotinib hydrochloride L-tartaric acid co-crystal Form I, as was confirmed by XRPD.

Example 8. Preparation of Nilotinib Hydrochloride L-Tartaric Acid Co-Crystal Form I A suspension of Nilotinib hydrochloride (1.0 g) and L-tartaric acid (0.5 g) in ethanol abs. (40 mL) was heated to reflux. The obtained solution was cooled to room temperature (RT) and stirred for about 2 h. The obtained precipitate was filtered to provide Nilotinib hydrochloride L-tartaric acid co-crystal Form I, as was confirmed by XRPD.

Example 9. Preparation of Nilotinib Hydrochloride L-Tartaric Acid Co-Crystal Form I Nilotinib hydrochloride (300 mg) and L-tartaric acid (160 mg) suspension in methanol/water 9:1 (10 mL) was dissolved at 70° C. The reaction mixture was stirred for 15 min at 70° C. and then cooled to RT. The obtained crystals were filtered, washed with methanol/water 9:1 and dried in a vacuum oven for 2 h at 50° C./10 mbar to provide Nilotinib hydrochloride L-tartaric acid co-crystal Form I, as was confirmed by XRPD.

Example 10. Preparation of Nilotinib Hydrochloride L-Tartaric Acid Co-Crystal Form II A suspension of Nilotinib hydrochloride form T17 (56.6 mg) and L-tartaric acid (15.0 mg) in tetrahydrofuran (1 mL) was stirred for 36 hours at 35° C. The solid was filtered and dried under vacuum at RT to obtain Nilotinib hydrochloride L-tartaric acid co-crystal Form II, as characterized by XRPD (FIG. 2).

Example 11. Preparation of Nilotinib Fumarate Form III

Nilotinib base (1.60 kg) and fumaric acid (0.40 kg) were suspended in 1-butanol (60 L). The reaction mixture was heated to about 95° C. and the obtained solution was filtered. The filtrate was cooled to 76-80° C. and seeded with Nilotinib fumarate Form III (64 g). The reaction mixture was stirred at 76-80° C. for 1 h, cooled to 48-52° C., stirred for 1 h, cooled to 8-12° C. and stirred for 4 hours. The obtained solid was filtered, washed twice with 1-butanol (23 L) and dried in a vacuum oven at 65-75° C. (LOD<1.0%). Nilotinib fumarate Form III was obtained as was confirmed by XRPD (1.61 kg).

Example 12. Preparation of Nilotinib Hydrochloride L-Tartaric Acid Co-Crystal Form I Nilotinib hydrochloride (10.0 g) and L-tartaric acid (5.3 g) were dissolved in ethanol, 96% (386 mL) at reflux. The solution was cooled to RT in 1 hour and stirred overnight. The solid was filtered, washed with ethanol, 96% and dried for 2 hours at 50° C./10 mbar. The obtained material corresponds to Nilotinib hydrochloride L-tartaric acid co-crystal Form I, as was confirmed by XRPD.

Example 13. Preparation of Nilotinib Hydrochloride L-Tartaric Acid Co-Crystal Form I Nilotinib hydrochloride (214.5 g) and L-tartaric acid (114.3 g) were dissolved in methanol/water (9:1 v/v) at 65° C. in a 6 L glass jacketed reactor. The solution was cooled down to 60° C. in 30 minutes, then to 45° C. in 40 min, then to 15° C. in 8 hours and finally to 5° C. in 16 hours. The suspension was filtered and washed with methanol/water (9:1 v/v). The product was dried for 4 hours at 50° C./10 mbar. The obtained material corresponds to Nilotinib hydrochloride L-tartaric acid co-crystal Form I, as was confirmed by XRPD.

Example 14. Preparation of Nilotinib Hydrochloride L-Tartaric Acid Co-Crystal Form I Nilotinib co-crystal Form I (30 g) (obtained in Example 13 was dried in a vacuum oven for about 8 hours at 100° C./100 mbar. XRPD of the obtained material corresponds to Nilotinib hydrochloride L-tartaric acid co-crystal Form I.

The invention claimed is:

1. A crystalline form of Nilotinib fumarate designated as Form III, characterized by
   an XRPD pattern having peaks at 5.5, 7.0, 11.0, 13.4 and 15.8 degrees two theta ±0.2 degrees two theta.

2. The crystalline Form III of Nilotinib fumarate according to claim 1, further characterized by data selected from one or more of the following:
   an FTIR spectrum having peaks at 3348, 1676, 1560, 1404 and 1296±4 cm$^{-1}$; or
   a Raman spectrum having peaks at 1668, 1614, 1407 and 1306±4 cm$^{-1}$; or
   a DSC endothermic peak of melting at about 228° C. (onset);
   or combinations of these data.

3. The crystalline Form III of Nilotinib fumarate according to claim 1, characterized by the XRPD pattern also having one, two, three, four, five, six or seven additional peaks selected from 14.0, 14.9, 16.3, 20.4, 20.5, 20.9 and 25.3 degrees two theta ±0.2 degrees two theta.

4. The crystalline Form III of Nilotinib fumarate according to claim 1, wherein the crystalline form is an anhydrous form.

5. A solid pharmaceutical composition comprising a crystalline form according to claim 1.

6. A solid pharmaceutical formulation comprising a crystalline form according to claim 1 and at least one pharmaceutically acceptable excipient.

7. A process for preparing the pharmaceutical formulation according to claim 6, comprising combining the crystalline form according to claim 1 with the at least one pharmaceutically acceptable excipient.

8. A process for preparing Nilotinib base or a Nilotinib salt or a solid state form of Nilotinib base or a Nilotinib salt comprising preparing crystalline Form III of Nilotinib fumarate, and converting it to Nilotinib base or a Nilotinib salt or a solid state form of Nilotinib base or a Nilotinib salt.

9. The process of claim 8, wherein the Nilotinib salt, or solid state form thereof, is Nilotinib hydrochloride or a solid state form thereof.

10. A crystalline form of Nilotinib fumarate designated as Form III, characterized by an XRPD pattern substantially as depicted in FIG. 1.

11. A crystalline form of Nilotinib fumarate designated as Form III, characterized by a solid state $^{13}$C NMR spectrum having characteristic peaks at 168.9, 159.1, 135.4 and 114.7±0.2 ppm.

12. A crystalline form of Nilotinib fumarate designated as Form III, characterized by a solid state $^{13}$C NMR spectrum substantially as depicted in FIG. 4.

13. A crystalline form of Nilotinib fumarate designated as Form III, characterized by a solid state $^{13}$C NMR spectrum having the following chemical shift absolute differences from a peak at 119.0 ppm ±1 ppm of 49.9, 40.1, 16.4 and −4.3 ppm ±0.1 ppm.

14. A crystalline form of Nilotinib fumarate designated as Form III, characterized by a solid state $^{13}$C NMR spectrum having chemical shift difference from a peak at 119.0 ppm ±1 ppm of 40.1 ppm ±0.1 ppm.

15. The crystalline Form III of Nilotinib fumarate according to claim 1, further characterized by FTIR spectrum substantially as depicted in FIG. 5.

16. The crystalline Form III of Nilotinib fumarate according to claim 1, further characterized by a Raman spectrum substantially as depicted in FIG. 6.

17. The crystalline Form III of Nilotinib fumarate according to claim 1, further characterized by a DSC thermogram substantially as depicted in FIG. 7.

18. The crystalline Form III of Nilotinib fumarate according to claim 1, further characterized by a TGA thermogram substantially as depicted in FIG. 8.

* * * * *